United States Patent
Shuber et al.

(12) 
(10) Patent No.: US 6,551,777 B1
(45) Date of Patent: Apr. 22, 2003

(54) METHODS FOR PRESERVING DNA INTEGRITY

(75) Inventors: Anthony P. Shuber, Milford; Frederick A. Huntress, Jr., Bolton; James K. Moore, Stow, all of MA (US)

(73) Assignee: Exact Sciences Corporation, Maynard, MA (US)

( * ) Notice: Subject to any disclaimer, the term of this patent is extended or adjusted under 35 U.S.C. 154(b) by 0 days.

(21) Appl. No.: 09/491,093

(22) Filed: Jan. 24, 2000

Related U.S. Application Data

(60) Provisional application No. 60/122,177, filed on Feb. 25, 1999.

(51) Int. Cl.[7] .......................... C12Q 1/68; C12P 19/34; C07H 21/04; C07H 21/00; C07H 21/02
(52) U.S. Cl. .................. 435/6; 435/91.2; 536/25.4; 536/25.41; 536/25.42; 536/23.3
(58) Field of Search ................. 435/6, 91.1, 91.2, 435/810; 436/94; 536/23.3, 24.31, 24.33, 25.3, 25.41, 25.4, 25.42

(56) References Cited

U.S. PATENT DOCUMENTS

| | | |
|---|---|---|
| 4,101,279 A | 7/1978 | Aslam |
| 4,309,782 A | 1/1982 | Paulin |
| 4,333,734 A | 6/1982 | Fleisher |
| 4,358,535 A | 11/1982 | Falkow et al. |
| 4,445,235 A | 5/1984 | Slover et al. |
| 4,535,058 A | 8/1985 | Weinberg et al. |
| 4,578,358 A | 3/1986 | Oksman et al. |
| 4,683,195 A | 7/1987 | Mullis et al. |
| 4,683,202 A | 7/1987 | Mullis |
| 4,705,050 A | 11/1987 | Markham |
| 4,735,905 A | 4/1988 | Parker |
| 4,786,718 A | 11/1988 | Weinberg et al. |
| 4,857,300 A | 8/1989 | Maksem |
| 4,871,838 A | 10/1989 | Bos et al. |
| 4,935,342 A | 6/1990 | Seligson et al. |
| 4,981,783 A | 1/1991 | Augenlicht |
| 4,982,615 A | 1/1991 | Sultan et al. |
| 5,087,617 A | 2/1992 | Smith |
| 5,126,239 A | 6/1992 | Livak et al. |
| 5,137,806 A | 8/1992 | LeMaistre et al. |
| 5,149,506 A | 9/1992 | Skiba et al. |
| 5,196,167 A | 3/1993 | Guadagno et al. |
| 5,200,314 A | 4/1993 | Urdea |
| 5,248,671 A | 9/1993 | Smith |
| 5,272,057 A | 12/1993 | Smulson et al. |
| 5,302,509 A | 4/1994 | Cheeseman |
| 5,330,892 A | 7/1994 | Vogelstein et al. |
| 5,331,973 A | 7/1994 | Fiedler et al. |
| 5,348,855 A | 9/1994 | Dattagupta et al. |
| 5,352,775 A | 10/1994 | Albertsen et al. |
| 5,362,623 A | 11/1994 | Vogelstein et al. |
| 5,369,004 A | 11/1994 | Polymeropoulos et al. |
| 5,378,602 A | 1/1995 | Polymeropoulos et al. |
| 5,380,645 A | 1/1995 | Vogelstein |
| 5,380,647 A | 1/1995 | Bahar |
| 5,382,510 A | 1/1995 | Levine et al. |
| 5,409,586 A | 4/1995 | Kamahori et al. |
| 5,416,025 A | 5/1995 | Krepinsky et al. |
| 5,458,761 A | 10/1995 | Kamahori et al. |
| 5,463,782 A | 11/1995 | Carlson et al. |
| 5,466,576 A | 11/1995 | Schulz et al. |
| 5,468,610 A | 11/1995 | Polymeropoulos et al. |
| 5,468,613 A | 11/1995 | Erlich et al. |
| 5,482,834 A | 1/1996 | Gillespie |
| 5,489,508 A | 2/1996 | West et al. |
| 5,492,808 A | 2/1996 | de la Chapelle et al. |
| 5,496,470 A | 3/1996 | Lenhart |
| 5,506,105 A | 4/1996 | Haydock |
| 5,508,164 A | 4/1996 | Kausch et al. |
| 5,512,441 A | 4/1996 | Ronal |

(List continued on next page.)

FOREIGN PATENT DOCUMENTS

| | | |
|---|---|---|
| AU | A-11325/95 | 4/1996 |
| CA | 2228769 | 2/1997 |
| DE | 195 30 123 A | 2/1997 |
| EP | 0 270 017 | 6/1988 |
| EP | 0 284 362 A3 | 9/1988 |
| EP | 0 284 362 A2 | 9/1988 |
| EP | 0 337 498 A2 | 10/1989 |
| EP | 0 390 323 A3 | 10/1990 |
| EP | 0 390 323 A2 | 10/1990 |
| EP | 0 391 565 A2 | 10/1990 |
| EP | 0 407 789 B1 | 1/1991 |
| EP | 0 407 789 A1 | 1/1991 |
| EP | WO-93/20235 | * 10/1993 |
| EP | 0 608 004 A2 | 7/1994 |
| EP | 0 259 031 B1 | 11/1994 |
| EP | 0 648 845 A | 4/1995 |
| EP | 0664339 | 7/1995 |
| EP | 0 664 339 A1 | 7/1995 |
| WO | WO 90/09455 | 8/1990 |
| WO | WO 92/13103 | 8/1992 |
| WO | WO 92/16657 | 10/1992 |
| WO | WO 93/18186 | 9/1993 |

(List continued on next page.)

OTHER PUBLICATIONS

Skoletsky J.E., et al. "High Frequency of Detecting Amplifiable DNA in Stools of Apparently Normal Individuals," *Gastroenterology*, Maynard, U.S.A. vol. 114, No. 4, p. A681 (1998).

International Search Report for International Patent Application Serial No. PCT/US99/27732, dated Nov. 7, 2001, 4 pages.

(List continued on next page.)

*Primary Examiner*—Remy Yucel
*Assistant Examiner*—Konstantina Katcheves
(74) *Attorney, Agent, or Firm*—Testa, Hurwitz & Thibeault, LLP

(57) ABSTRACT

Methods for extracting DNA from a biological sample that result in a higher yield of target DNA than conventional methods. More particularly, methods for extracting DNA include exposing the biological sample to inhibitors of DNA degradation.

11 Claims, 5 Drawing Sheets

U.S. PATENT DOCUMENTS

| | | |
|---|---|---|
| 5,514,547 A | 5/1996 | Balazs et al. |
| 5,527,676 A | 6/1996 | Vogelstein et al. |
| 5,532,108 A | 7/1996 | Vogelstein |
| 5,538,851 A | 7/1996 | Fach et al. |
| 5,559,014 A | 9/1996 | Estes et al. |
| 5,580,729 A | 12/1996 | Vogelstein |
| 5,589,335 A | 12/1996 | Kearney et al. |
| 5,612,473 A | 3/1997 | Wu et al. |
| 5,635,352 A | 6/1997 | Urdea et al. |
| 5,641,628 A | 6/1997 | Bianchi |
| 5,670,325 A | 9/1997 | Lapidus et al. |
| 5,688,643 A | 11/1997 | Oka et al. |
| 5,709,998 A | 1/1998 | Kinzler et al. |
| 5,741,650 A | 4/1998 | Lapidus et al. |
| 5,759,777 A | 6/1998 | Kearney et al. |
| 5,830,665 A | 11/1998 | Shuber et al. |
| 5,846,710 A | 12/1998 | Bajaj |
| 5,856,104 A | 1/1999 | Chee et al. |
| 5,888,778 A | 3/1999 | Shuber |
| 5,910,407 A * | 6/1999 | Vogelstein et al. |
| 5,916,744 A | 6/1999 | Taylor |
| 5,928,870 A | 7/1999 | Lapidus et al. |
| 5,952,178 A | 9/1999 | Lapidus et al. |
| 6,020,137 A | 2/2000 | Lapidus et al. |
| 6,037,465 A | 3/2000 | Hillebrand et al. |
| 6,100,029 A | 8/2000 | Lapidus et al. |
| 6,143,529 A | 11/2000 | Lapidus et al. |
| 6,146,828 A | 11/2000 | Lapidus |
| 6,177,251 B1 | 1/2001 | Vogelstein et al. |
| 6,203,993 B1 | 3/2001 | Lapidus et al. |
| 6,214,558 B1 | 4/2001 | Shuber et al. |
| 6,268,136 B1 | 7/2001 | Shuber et al. |
| 6,280,947 B1 | 8/2001 | Shuber et al. |
| 6,300,077 B1 | 10/2001 | Shuber et al. |
| 6,303,304 B1 | 10/2001 | Shuber et al. |
| 2001/0018180 A1 | 8/2001 | Shuber et al. |

FOREIGN PATENT DOCUMENTS

| | | |
|---|---|---|
| WO | WO 93/20233 | 10/1993 |
| WO | WO 93/20235 | 10/1993 |
| WO | WO 94/00603 | 1/1994 |
| WO | WO 94/01447 | 1/1994 |
| WO | WO 94/09161 | 4/1994 |
| WO | WO 94/10575 | 5/1994 |
| WO | WO 94/11383 | 5/1994 |
| WO | WO 95/07361 | 3/1995 |
| WO | WO 95/09928 | 4/1995 |
| WO | WO 95/09929 | 4/1995 |
| WO | WO 95/12606 | 5/1995 |
| WO | WO 95/13397 | 5/1995 |
| WO | WO 95/15400 | 6/1995 |
| WO | WP 95/16792 | 6/1995 |
| WO | WO 95/18818 | 7/1995 |
| WO | WO 95/19448 | 7/1995 |
| WO | WO 95/25813 | 9/1995 |
| WO | WO 95/31728 | 11/1995 |
| WO | WO 96/01907 | 1/1996 |
| WO | WO 96/06951 | 3/1996 |
| WO | WO 96/08514 | 3/1996 |
| WO | WO 96/12821 | 5/1996 |
| WO | WO 96/13611 | 5/1996 |
| WO | WO 96/30545 | 10/1996 |
| WO | WO 97/07239 | 2/1997 |
| WO | WO 97/09449 | 3/1997 |
| WO | WO 97/09600 A2 | 3/1997 |
| WO | WO 97/09600 A3 | 3/1997 |
| WO | WO 97/23651 | 7/1997 |
| WO | WO 97/25442 | 7/1997 |
| WO | WO 97/28450 | 8/1997 |
| WO | WO 98/08971 | 3/1998 |
| WO | WO 98/38338 | 9/1998 |
| WO | WO 98/39478 | 9/1998 |
| WO | WO 98/58081 | 12/1998 |
| WO | WO 98/58084 | 12/1998 |
| WO | WO 99/07894 | 2/1999 |
| WO | WO 99/20798 | 4/1999 |
| WO | WO 99/28507 | 6/1999 |
| WO | WO 99/53316 | 10/1999 |
| WO | WO 99/55912 | 11/1999 |
| WO | WO 99/66077 | 12/1999 |
| WO | WO 00/09751 | 2/2000 |
| WO | WO 00/11215 | 3/2000 |
| WO | WO 00/31298 | 6/2000 |
| WO | WO 00/31303 | 6/2000 |
| WO | WO 00/31305 | 6/2000 |
| WO | WO 00/32820 | 6/2000 |
| WO | WO 00/50640 | 8/2000 |
| WO | WO 00/58514 | 10/2000 |
| WO | WO 00/61808 | 10/2000 |
| WO | WO 00/66005 | 11/2000 |
| WO | WO 00/70096 | 11/2000 |
| WO | WO 01/11083 | 2/2001 |
| WO | WO 01/18252 | 3/2001 |
| WO | WO 01/42502 | 6/2001 |
| WO | WO 01/42503 | 6/2001 |
| WO | WO 01/42781 | 6/2001 |
| WO | WO 01/64950 | 9/2001 |

OTHER PUBLICATIONS

Watson et al. (Sep. 1994) "Isolation of Differentially Expressed Sequence Tags From Human Breast Cancer," *Cancer Res.* 54(17):4598–4602.

Ausubel et al., (1995), *Short Protocols in Molecular Biology*, 3d ed., pp. 2–3–2–12, 3–30–3–33.

Blum H.E., (1995) "Colorectal Cancer: Future Population Screening for Early Colorectal Cancer" *European Journal of Cancer*, vol. 31A, pp. 1369–1372.

Boom et al., (Mar. 1990) "Rapid and Simple Method for Purification of Nucleic Acids" *J. Clin. Microbiol.*, vol. 28, No. 3, pp. 495–503.

Bos et al., (May 28, 1987) "Prevalence of ras Gene Mutations in Human Colorectal Cancers," *Nature,* vol. 327, pp. 293–297.

Caldas et al., (Jul. 1, 1994) "Detection of K–ras Mutations in the Stool of Patients with Pancreatic Adenocarcinoma and Pancreatic Ductual Hyperplasia" *Cancer Research,* vol. 54, pp. 3568–3573.

Cave et al., (1994) "Reliability of PCR Directly from Stool Samples: Usefulness of an Internal Standard," *BioTechniques,* vol. 16, No. 5, pp. 809–810.

Charlesworth et al., (Sep. 15, 1994) "The Evolutionary Dynamics of Repetitive DNA in Eukaryotes," *Nature,* vol. 371, pp. 215–220.

Coombs et al., (May 21, 1996) "A Rapid, Simple, and User–Friendly Method for DNA Extraction from Clinical Stool Samples," *ASM 1996 General Meeting,* New Orleans, LA.

Chen et al., (Jul. 15, 1996), "Detection of Single–Base Mutations by a Competitive Mobility Shift Assay," *Analytical Biochemistry, US, Academic, Press,* vol. 239, No. 1, pp. 61–69.

Cohen, S., (Mar. 22, 1996) "Human Nucleic Acid Extraction from Stool and Hybridization Protocols" (3 pages).

Coll et al., (Oct. 1989) "Evaluation of a Rapid Method of Extracting DNA from Stool Samples for Use in Hybridization Assays," *Journal of Clinical Microbiology,* vol. 27, No. 10, pp. 2245–2248.

Cunningham C. and M.G. Dunlop, (1996) "Molecular Genetic Basis of Colorectal Cancer Susceptibility," *British Journal of Surgery,* vol. 83, pp. 321–329.

Deng et al., (Dec. 20, 1996) "Loss of Heterozygosity in Normal Tissue Adjacent to Breast Carcinomas," *Science,* vol. 274, pp. 2057–2059.

Deuter et al., (1995) "A method for Preparation of Fecal DNA Suitable for PCR," *Nucleic Acids Research,* vol. 23, No. 18, pp. 3800–3801.

Dib et al., (Mar. 14, 1996) "A Comprehensive Genetic Map of the Human Genome Based on 5,264 Microsatellites," *Nature* vol. 380, pp. 152–154.

Duffy M.J., (1995) "Can Molecular Markers Now be Used for Early Diagnosis of Malignancy?" *Clin. Chem,.* vol. 41, No. 10, pp. 1410–1413.

Echeverria et al., (Sep. 1985) "DNA Hybridization in the Diagnosis of Bacterial Diarrhea," *Clinics in Laboratory Medicine,* vol. 5, No. 3, Sep. 1985, pp. 447–462.

Eguchi et al., (Apr. 15, 1996) "Mutations of the p53 Gene in the Stool of Patients with Resectable Colorectal Cancer," *Cancer Supplement,* vol. 77, No. 8, pp. 1707–1710.

Enari et al., (Jan. 1, 1998) "A Caspase–Activated DNase that Degrades DNA During Apoptosis, and its Inhibitor ICAD," *Nature,* vol. 391, pp. 43–50.

Fearon E.R., (1995) "16 Molecular Abnormalities in Colon and Rectal Cancer," *The Molecular Basis of Cancer,* pp. 340–357.

Gull Laboratories, Inc. (1996) XTRAX DNA Extraction Kit (Information Sheet), pp. 1–3.

Gyllensten U.B., Allen M., (1995) "Sequencing of In Vitro Amplified DNA," *Recombinant DNA Methodology II,* (Wu, ed.), pp. 565–578.

Hasegawa et al., (1995) "Detection of K–ras Mutations in DNAs Isolated From Feces of Patients with Colorectal Tumors by Mutant–Allele–Specific Amplification (MASA)," *Oncogene,* vol. 10, pp. 1441–1445.

Honchel et al., (1995) "Genomic Instability in Neoplasia," *Seminars in Cell Biology,* vol. 6, pp. 45–52.

Hoss et al., (Sep. 17, 1992) "Excrement Analysis by PCR" *Scientific Correspondence* pp. 199.

Hunsaker, et al. (1989), "Use of Reversible Target Capture to Detect Subattomole Quantities of Target Nonradioleotopically in Crude Specimens in One Hour," *Abstracts of the 89th Meeting of the American Society for Microbiology,* D–169, p. 110.

Jessup J.M. and G.E. Gallick, (Sep./Oct. 1992) "The Biology of Colorectal Carcinoma," *Current Problems in Cancer* pp. 263–328.

Jonsson et al., (Jan. 1995) "From Mutation Mapping to Phenotype Cloning," *Proc. Natl. Acad. Sci.,* vol. 92 pp. 83–85.

Lefrere et al., (Oct. 1998) "Screening Blood Donations for Viral Genomes: Multicenter Study of Real–Time Simulation Using Pooled Samples on the Model of HCV RNA Detection" *Transfusion,* vol. 38, pp. 915–923.

Lengauer et al., (Dec. 17, 1998) "Genetic Instabilities in Human Cancers," *Nature,* vol. 396, pp. 643–649.

Leong et al., (1993) "Detection of MYCN Gene Amplification and Deletions of Chromosome 1p in Neuroblastoma by In Situ Hybridization Using Routine Histologic Sections," *Laboratory Investigations,* vol. 69, No. 1, pp. 43–50.

Li et al., (Aug. 1996) "Rapid Detection of Mycobacterium Avium in Stool Samples from AIDS Patients by Immunomagnetic PCR," *J. Clin. Microbiol.,* vol. 34, No. 8, pp. 1903–1907.

Litia et al., (1992) "Simultaneous Detection of Two Cystic Fibrosis Alleles Using Dual–Label Time–Resolved Fluorometry," *Molecular and Cellular Probes,* vol. 6, pp. 505–512.

Loktionov A. and I. K. O'Neill, (1995) "Early Detection of Cancer–Associated Gene Alterations in DNA Isolated from Rat Feces During Intestingal Tumor Induction with 1,2–Dimethylhydrazine," *International Journal of Oncology,* vol. 6, pp. 437–445.

Loktionov et al., (Feb., 1998) "Quantitation of DNA from Exfoliated Colonocytes Isolated from Human Stool Surface as a Novel Noninvasive Screening Test for Colorectal Cancer," *Clinical Cancer Research,* vol. 4, pp. 337–341.

Mao L. et al., (Feb. 2, 1996) "Molecular Detection of Primary Bladder Cancer by Microsatellite Analysis," *Science,* vol. 271, pp. 659–662.

Morandi et al., (Jun. 1998) "Detection of HIV Type 1 RNA in Pools of Sera Negative for Antibiotics to HIV–1 and HIV–2," *J. of Clinical Microbiology,* vol. 36, No. 6, pp. 1534–1538.

Morrissey et al., (May 14–18, 1989) "Novel Hybridization Technique with Subattomole Sensitivity in Specimens" *American Society for Microbiology,* 89th Annual Meeting, Abstract D–168, p. 110.

Morrissey, et al., (Sep. 1989) "Nucleic Acid Hybridization Assays Employing dA–Tailed Capture Probes," *Analytical Biochemistry,* vol. 181, No. 2, pp. 345–359.

Morrissey, D. and Mark Collins, (Jun. 1989) "Nucleic Acid Hybridization Assays Employing dA–Tailed Capture Probes. Single Capture Methods," *Mol. And Cell. Probes,* vol. 3, No. 2, pp. 189–207.

Myers, R.M., (Feb. 12, 1993) "The Pluses of Subtraction," *Science,* vol. 259, pp. 942–943.

Naber S.P., (Dec. 1, 1994) "Molecular Pathology—Detection of Neoplasia," *New England Journal of Medicine,* vol. 331, No. 22, pp. 1508–1510.

Nollau et al., (May 1996) "Isolation of DNA from Stool and Bodily Fluids for PCR Amplication," *BioTechniques,* vol. 20, No. 5, pp. 784–788.

Nollau et al., (1996) "Detection of K–ras Mutations in Stools of Patients with Colorectal Cancer by Mutant–Enriched PCR," *Int. J. Cancer,* vol. 66 pp. 332–336.

Olive, (Feb. 1989) "Detection of Enterotoxigenic *Escherichia coli* after Polymerase Chain Reaction Amplification with a Thermostable DNA Polymerase," *Journal of Clinical Microbiology,* vol. 27, No. 2, pp. 261–265.

Orlow I., et al., (Oct. 18, 1995) "Deletion of the p16 and p15 Genes in Human Bladder Tumors *Journal of the National Cancer Institute,,*" vol. 87, No. 20, pp. 1524–1529.

Paabo et al., (1988) "Mitochondrial DNA Sequences from a 7000–year old Brain," *Nucleic Acids Research,* vol. 16, No. 20, pp. 9775–9777.

Pacek et al., (May 1993) "Determination of Allele Frequencies at Loci with Length Polymorphism by Quantitive Analysis of DNA Amplified from Pooled Samples," *PCR Methods and Applications,* vol. 2, No. 4, pp. 313–317.

Piao et al., (Sep 1997) "Relationship between Loss of Heterozygosity of Tumor Suppressor Genes and Histologic Differentiation in Hepatocellular Carcinoma," *Cancer*, vol. 80, No. 5, pp. 865–872.

Raff, M., (Nov. 12, 1998) "Cell Suicide for Beginners," *Nature*, vol. 396, pp. 119–122.

Ravelingien et al., (1995) "Contribution of Molecular Oncology in the Detection of Colorectal Carcinomas," *Acta Gastro–Enterologica Belgica*, vol. 58, pp. 270–273.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240–251.

Ridanpaa et al., (1995) "Detection of Los of Heterozygosity in the p53 Tumor Suppressor Gene Using a PCR–based Assay," *Path. Res. Pract.*, vol. 191, pp. 399–402.

Ruzicka et al., (1992) "Apolipoprotein Allele Specific PCR: Large–Scale Screening of Pooled Blood Samples," *J. of Lipid Research*, vol. 33, pp. 1563–1567.

Sanger et al., (Dec. 1977) "DNA Sequencing with Chain–Terminating Inhibitors" *Proc. Natl. Acad. Sci. USA*, vol. 74, No. 12, pp. 5463–5467.

Segel I., (1976), "Double Label Analysis," *Biochemical Calculations*, 2d ed., pp. 373–376.

Shaw et al., (1998) "Allele Frequency Distribution in Pooled DNA Samples, Applications to Mapping Complex Disease Genes," *Genome Research*, vol. 8, pp. 111–123m.

Sidransky, et al., (Apr. 3, 1992) "Identification of ras Oncogene Mutations in the Stool of Patients with Curable Colorectal Tumors," *Science*, vol. 256, pp. 102–105.

Smith–Ravin et al., (1995) "Detection of c–Ki–ras Mutations in Faecal Samples from Sporadic Colorectal Cancer Patients," *Gut*, vol. 36, pp. 81–86.

Supplemental Information, ProCipitate and Cleanascite, LigoChem, Inc., Fairfield, NJ (date unknown).

Takeda et al., (1993) "Detection of K–ras Mutation in Sputum by Mutant–Allele–Specific Amplification (MASA)," *Human Mutation*, vol. 2, pp. 112–117.

Thibodeau et al., (May 7, 1993) "Microsatellite Instability in Cancer of the Proximal Colon," *Science*, vol. 260, pp. 816–819.

Tompkins et al., (1986) "Approaches to the Detection of Enteric Pathogens, Including Campylobacter, using Nucleic Acid Hybridization," *Diagn. Microbiol, Infect. Dis.*, vol. 4, pp. 715–785.

Vera–Garcia, et al., (May 16–20, 1993) "Development and Evaluation of an Instrument Designed to Reproducibly Release Nucleic Acids from Microorganisms" *American Society for Microbiology: Polymerase Chain Reaction*, 93$^{rd}$ General Meeting, Session 214, Abstract C–217, p. 484.

Villa et al., (May 1996) "Identification of Subjects at Risk for Colorectal Carcinoma Through a Test Based on K–ras Determination in the Stool," *Gastroenterology*, vol. 100, No. 5, pp. 1346–1353.

Vogelstein, B. and Kinzler, K.W., (Aug., 1999) "Digital PCR," *Proc. Natl. Acad. Sci. USA*, vol. 96, pp. 9236–9241.

Vogelstein et al., (1979) "Preparative and Analytical Purification of DNA from Agarose," *Proc. Natl. Acad. Sci. USA*, vol. 76, No. 2, pp. 615–619.

Wallace et al., (1979) "Hybridization of Synthetic Oligodeoxyribonucleotides to $\Phi\chi$ 174 DNA: the Effect of Single Base Pair Mismatch," *Nucleic Acids Research*, vol. 6, No. 11, pp. 3543–3557.

Walsh et al., (1991) "Chelex® 100 as a Medium for Simple Extraction of DNA for PCR–Based Typing from Forensic Material," *BioTechniques*, vol. 10, No. 4, pp. 506–513.

Walsh et al., (Feb. 6, 1992) "Preferential PCR Amplification of Alleles: Mechanisms and Solutions," *PCR Methods and Applications*, pp. 241–250.

Walton et al., (1997) "A PCR–Based Method for Detecting Rare Genotypes in Large Samples of Individuals," *Mol. Ecology*, vol. 6, No. 2, pp. 195–197.

Wang et al., (May 15, 1998) "Large–Scale Identification, Mapping, and Genotyping of Single–Nucleotide Olymorphisms in the Human Genome," *Science*, vol. 280, pp. 1077–1082.

Watson et al., "Isolation of Differentiality Expresseed Sequence Tags from Human Breast Cancer," *Advances in Brief XP 000576043*, pp. 4598–4602.

Young G.P., and B.H. Demediu, (1992) "The Genetics, Epidemiology, and Early Detection of Gastrointestinal Cancers" *Current Opinion in Oncology*, vol. 4, pp. 728–735.

Metspalu A., "Arrayed Primer Extension (APEX) for Mutation Detection Using Gene–Specific DNA Chips" *European Journal of Human Genetics*, vol. 6, No. Supp 1, 1998, p. PL36 XP000892253 Abstract.

Santagati et al., "Quantitation of low abundance mRNAs in glial cells using different polymerase chain reaction (PCR)–based methods" *Brain Research Protocols*, vol. 1, 1997, pp. 217–223, XP000892447.

Pharmacia, (1998) *BioDirectory*, pp. 104–109.

Pharmacia, (1991/1992) *Molecular and Cell Biology Catalogue*, pp. 8.3–8.6.

Samiotaki *et al.* (1994), "Dual–Color Detection of DNA Sequence Variants by Ligase–Mediated Analysis," *Genomics* 20:238–42.

Rinaldy *et al.* (1988), "Gene Cloning Using cDNA Libraries in a Differential Competition Hybridization Strategy: Application to Cloning XP–A Related Genes," *DNA* 7(8):563–70.

Azhikina *et al.* (1996), "Factors Affecting the Priming Efficiency of Short Contiguous Oligonucleotide Strings in the Primer Walking Strategy of DNA Sequencing," *DNA Sequence* 6:211–16.

\* cited by examiner

US 6,551,777 B1

METHODS FOR PRESERVING DNA INTEGRITY

CROSS-REFERENCE TO RELATED APPLICATION

The present application claims priority to and the benefit of U.S. provisional patent application Ser. No. 60/122,177, filed Feb. 25, 1999, the entire disclosure of which is incorporated herein by reference.

TECHNICAL FIELD

The invention provides methods for deoxyribonucleic acid ("DNA") extraction from a biological sample. More particularly, the invention relates to methods for high yield DNA extraction from a heterogeneous biological sample by inhibiting DNA degradation.

BACKGROUND OF THE INVENTION

DNA is a relatively stable molecule that is routinely isolated from biological samples. Recently, many diseases involving instabilities (e.g., mutations) in genomic DNA have been characterized. Also, many pathogens have been identified by the presence or absence of a particular DNA in a biological sample. Many diseases, such as cancer, are optimally detected early in their progression. In order for early detection to be effective, relatively low levels of DNA which are indicative of cancer must be detected against a high background of other DNA (e.g., normal human DNA, bacterial DNA, etc.). This type of detection is technically difficult and typically results in low sensitivity of detection. Moreover, in certain complex specimens, including stool, what little species-specific DNA exists, is rapidly degraded, making efficient sequence-specific detection even more difficult. Thus, a need exists for methods to retain integrity of DNA in a sample, especially in samples in which the DNA to be detected is in low proportion relative to other DNA in the sample and is degraded quickly.

SUMMARY OF THE INVENTION

The present invention provides methods for preserving the integrity of DNA in a sample. In a preferred embodiment, methods of the invention prevent enzyme-mediated DNA degradation. Preservation of DNA integrity facilitates isolation and detection of DNA.

Methods of the invention are especially useful for extracting or detecting DNA in a biological specimen, especially one that contains low levels of relevant DNA. A good example of a specimen that contains lower-levels of relevant DNA is stool. Typical human stool contains only small amounts of intact human DNA. Most of the human DNA in stool from a healthy individual is presumably from exfoliated epithelial cells, and has undergone apoptotic degradation. As the forming stool passes through the colon, colonic epithelial cells are sloughed onto the stool as part of the cellular turnover that occurs in the colon. Stool also contains sloughed cells from other luminal sources (e.g., lung, stomach, esophagus, etc.) Sloughed cells typically have undergone or are undergoing apoptosis, leaving cellular DNA in small fragments. Enzymes, such as deoxyribonuclease ("DNase") and Micrococcal nuclease contribute to the degradation of any intact human DNA that remains. Prior art methods, while using DNase inhibitors, have failed to achieve significant yields of intact, species-specific DNA from stool. Therefore, such methods failed to consider optimization of inhibition of DNA degradation. Methods of the invention are based on the realization that optimal inhibition of DNA degrading enzyme(s) effectively preserves DNA, especially large, diagnostically-relevant DNA fragments that are present in a sample.

In one aspect, the invention comprises inhibiting nucleic acid degradation in a sample and optionally extracting a target DNA with, for example, a phenol-chloroform extraction. Preferably, the inhibition of nucleic acid degradation is sufficient to produce a critical number of molecules of analyzable DNA. In one embodiment, methods of the invention comprise inhibiting an enzyme capable of DNA degradation in a stool sample. In a preferred embodiment, methods of the invention comprise exposing a stool sample to an ion chelator, such as a divalent ion chelator. Ion chelators, in certain embodiments inhibit DNase. Examples of preferred inhibitors include ethylenediaminetetraacetic acid ("EDTA"). Additional preferred methods of the invention comprise exposing a stool sample to a Micrococcal nuclease inhibitor, such as EGTA, also a divalent ion chelator. Inhibitors of DNA degradation may be used either alone or in combination to achieve optimal levels of DNA preservation.

Methods of the invention are practiced using any inhibitor of DNA degradation. The amount of inhibitor varies depending on the inhibitor that is used. However, an inhibitor must be used in an amount that preserves significant levels of DNA in the sample for subsequent analysis. Methods for determining sufficient levels of DNA are presented below. Such methods allow the skilled artisan to practice the invention with specificity regardless of the inhibitor used. According to preferred methods, an amount of inhibitor is used that preserves sufficient DNA in the sample for detection of a target DNA within a desired level of statistical confidence. Using methods described herein, the skilled artisan can determine an appropriate amount of any inhibitor for use in methods of the invention. The use of various specific inhibitors is exemplified below.

In another preferred embodiment, methods of the invention comprise obtaining a representative (circumfrential or cross-sectional) stool sample, exposing the sample or a portion thereof to a DNase inhibitor, and isolating DNA from the sample. One preferred DNase inhibitor is EDTA. Preferred amounts of EDTA are from about 0.042 g per gram of stool to about 0.782 g per gram of stool and especially from about 0.250 g per gram of stool to about 0.521 g per gram of stool. DNA may be extracted, for example, by a phenol-chloroform extraction. After extraction, the DNA may be analyzed by methods known in the art. For example, U.S. Pat. No. 5,830,665 and U.S. Pat. No. 5,670,325, which are incorporated by reference herein, disclose methods for analyzing DNA which has been extracted from a stool sample.

Methods of the invention are useful in any sample in which inhibition of DNA degradation is desired. For example, methods of the invention are especially effective in samples comprising exfoliated cells, especially exfoliated epithelial cells. The DNA contained in such samples typically degrades rapidly, making analysis of a particular DNA, especially one that exists in low proportion within the sample, difficult. For example, such samples include stool, sputum, urine, pus, and collostrum. Methods of the invention include inhibiting DNA degradation in such samples, thus preserving a sufficient amount of DNA for specific, sensitive detection. Any of the features described above, such as DNA degradation inhibitors or amounts of inhibitors that are used, can be useful in samples containing exfoliated cells.

DETAILED DESCRIPTION OF THE INVENTION

I. Introduction

The present invention provides methods for increased yield of DNA in a biological sample by preserving the integrity of DNA in the sample. Such methods are especially useful when the DNA of interest ("the target DNA") is present in the sample at a low frequency, or is rapidly degraded. More particularly, methods of the invention include, for example, inhibiting enzymes that degrade DNA.

Prior to the present invention, those skilled in the art have not been concerned with preventing DNA degradation prior to extraction from a sample. Typically, either the DNA of interest is present in samples in relatively large quantities (e.g., tumor cells, blood), or methods are directed toward increasing sensitivity to low-frequency DNA, and not to preserving its integrity. However, especially in the case of low-frequency DNA in a heterogeneous sample (e.g., a sample having cells and/or cellular debris from multiple cell types and/or organisms), methods for increasing sensitivity to DNA have not been entirely successful. Methods of the invention provide a new approach by preserving the integrity of DNA. Methods of the invention increase the likelihood of detecting a specific target DNA, because such methods make more intact target DNA available in the sample.

Figure 1:
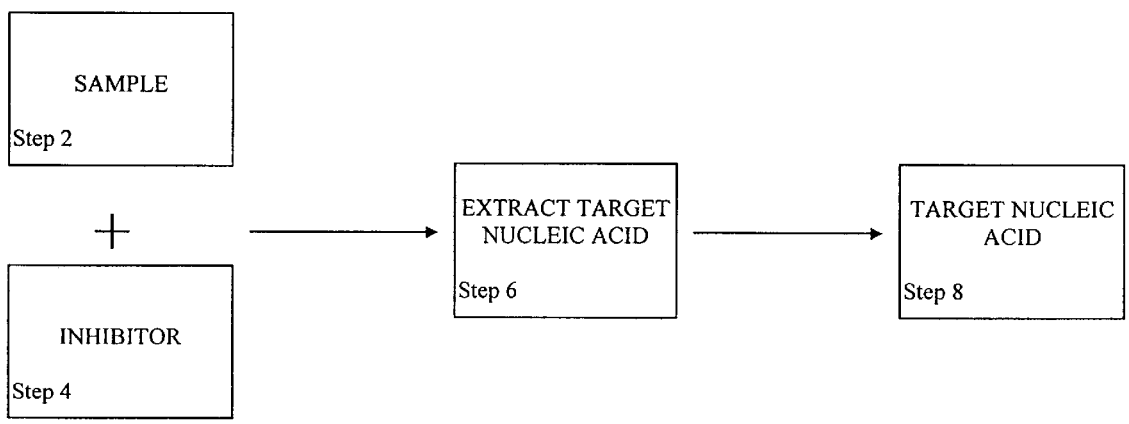
FIG. 1 shows a flow chart describing one aspect of the invention.

Referring to FIG. 1, one generalized method of the invention involves obtaining a sample (step 2) and exposing it to a DNA degradation inhibitor (step 4). Once the sample has been exposed to the DNA degradation inhibitor, target DNA is extracted (step 6). The presence or absence of this extracted target DNA is then detected (step 8).

In heterogeneous samples, such as stool, endogenous human DNases and/or bacterial nucleases degrade DNA. Examples of nucleases include DNases, such as deoxyribonuclease I ("DNase I") and Micrococcal nuclease. DNase and Micrococcal nuclease both require a divalent cation to function optimally. For DNase, suitable ions include $Mn^{+2}$ and $Mg^{+2}$. For Micrococcal nuclease, $Ca^{+2}$ is a suitable ion. Ion chelators, and particularly divalent ion chelators, are capable of inhibiting nucleases. Ion chelators remove ions from association with the nuclease, thus inhibiting the nuclease's function. For example, EDTA or EGTA used in optimal amounts are useful ion chelators for use in the present invention.

Other compounds that inactivate, interfere with, or slow enzyme-mediated degradation of DNA are useful. For example, ligands and/or antibodies which compete for or interfere with the active site of DNA degrading enzymes, which inactivate those enzymes, and/or which block messenger systems that control DNA degrading enzymes are useful in the practice of the invention. Phenol-chloroform extraction components, at higher concentrations than those typically used during extraction, also are capable of inhibiting nucleases by separation and denaturation. For example, phenol denatures DNA degradation enzymes, and is used in methods of the invention to preserve DNA integrity. Also, proteinases which degrade and/or denature DNA degrading enzymes are useful.

Methods of the invention comprise the use of optimal amounts of DNA degradation inhibitors in order to preserve high-integrity DNA sufficient for diagnostic screening. In heterogeneous samples, such as stool, target DNA (e.g., mutated DNA or reductions in enumerated wild type DNA that are indicative of a mutation) is present in low amounts. An optimal amount of a DNA degradation inhibitor is an amount that results in a measurable improvement in the quantity of DNA available in the sample. Thus, the skilled artisan can empirically determine optimal amounts of DNA degradation inhibitors for use in methods of the invention by using inhibitor amounts necessary to preserve a diagnostically-relevant fraction of high-integrity target DNA. A method for determining diagnostically-relevant DNA amounts is presented below.

Amplification of DNA, and other stochastic processes, performed on heterogeneous samples may actually contribute to the inability to measure low-frequency DNA. For example, a typical cancer-associated (mutant) DNA in the early stages of oncogenesis represents about 1% of the DNA in a heterogeneous sample (e.g., stool). If DNA in the sample is amplified at 30% PCR efficiency, any particular DNA has only a 30% chance of being amplified in any round of PCR. Thus, if a mutant DNA initially present as 1% of a sample is not amplified in the first round, the mutant DNA will represent only about 0.7% of the DNA in the sample after round 1.

If no mutant is amplified in the first two rounds (0.7×0.7, or a 49% probability), the mutant DNA will represent only about 0.6% of the DNA in the sample going into round three of the PCR. If the post-amplification assay used to detect the mutant has a sensitivity of no more than 0.5% for the mutant, it may not be possible to reliably detect the presence of the mutant DNA. Thus, the detection method itself may actually contribute to difficulties in detecting low-frequency DNA, especially if sufficient amounts of intact DNA are not present in a sample. Thus, one means for determining an appropriate amount of inhibitor to use in methods of the invention is to determine the minimum amount of intact DNA that must be present in a sample to avoid the stochastic effects described above, and then to use sufficient inhibitor to produce at least the minimum number of DNA molecules in the sample. Methods for calculating the minimum number of DNA molecules necessary to overcome the effects of stochastic processes, such as PCR, are presented below.

A model useful to generate sufficient DNA molecules for accurate measurement operates by iterating stochastic processes over a number of rounds of PCR. In the context of molecular disease diagnostics, the model dictates the number of molecules that must be presented to the PCR in order to reliably ensure amplification of desired target DNA. The model incorporates a preset PCR efficiency (established to meet separate specificity requirements), and a preset ratio of mutant DNA to total DNA in the sample to be analyzed (which is a property of the disease to be detected and the nature of the sample). Based upon those input values, the model predicts the number of molecules that must be presented to the PCR in order to ensure, within a predefined level of statistical confidence, that a low-frequency (target) molecule will be amplified and detected. Once the number of molecules is determined, the skilled artisan can determine the sample size to be used (e.g., the weight, volume, etc.), depending on the characteristics of the sample (e.g., its source, molecular makeup, etc.). The model dictates the number of molecules that must be presented to the PCR in order to reliably ensure amplification and detection.

The exemplary model simulates selection of DNA for amplification through several rounds of PCR. For purposes of the model, a sample is chosen that contains a ratio of mutant-to-total DNA of 1:100, which is assumed to lie at the clinical threshold for disease. For example, in colorectal cancer 1% of the human DNA in a specimen (e.g., stool) is mutated (i.e., has a deletion, substitution, rearrangement, inversion, or other sequence that is different than a corresponding wild-type sequence). Over a large number of PCR rounds, both the mutant and wild-type molecules will be selected (i.e., amplified) according to their ratio in the specimen (here, nominally 1 in 100), assuming there are any abnormal molecules in the sample. However, in any one round, the number of each species that is amplified is determined according to a Poisson distribution. Over many rounds, the process is subject to stochastic errors that reduce the ability to detect low-frequency mutant DNA. However, the earlier rounds of PCR (principally, the first two rounds) are proportionately more important when a low-frequency species is to be detected, and any rounds after round 10 are virtually unimportant. Thus, the model determines the combined probability of (1) sufficient mutant molecules being presented to the PCR, and (2) the effects of stochastic amplification on those molecules so that at the output of the PCR there will be a sufficient number of molecules and a sufficient ratio of mutant to total molecules to assure reliable detection.

The model used to run the number of molecules necessary at the first round of PCR was generated as a "Monte Carlo" simulation of a thousand experiments, each experiment consisting of 10 cycles of PCR operating on each molecule in the sample. The simulation analyzed (1) taking a sample from the specimen; and (2) each round of PCR iteratively to determine whether, for each round, a mutant DNA if present in the sample was amplified. Upon completion of the iterative sampling, the model determined the percent of rounds in which a mutant strand was amplified, the percent of mutants exceeding a predetermined threshold for detection (in this example 0.5% based upon the mutant:total ratio of 1%), the coefficient of variation (CV) for stochastic sampling in each round alone, and the coefficient of variance for stochastic sampling and PCR in combination.

Stochastic noise is created in PCR if the PCR efficiency is anything other than 0% or 100% (these two cases represent either there is no amplification at all or perfect fidelity of specific amplification). The noise, or background, signal level in a PCR that is between 0% and 100% varies with the efficiency of the PCR. The standard deviation of stochastic noise, S, in a PCR is given by the equation, $S=\sqrt{npq}$, where n is the number of molecules in the sample, p is the efficiency of PCR, and q is $1-p$. Table 1 presents results obtained for iterative samplings with PCR efficiency set at 100% and 20%, and a mutant:total ratio of 0.5%.

Table 1 represents output from the model in 12 experiments conducted under various conditions. The first row shows the nominal number of molecules entering the first round of PCR (i.e., the total number of molecules available for amplification). The second row shows the percent of molecules (DNA) in the biological specimen that is expected to be mutant. For colorectal cancer indicia in DNA recovered from stool, the threshold for clinical relevance in the detection of early stage cancer is 1%. That is, 1% of the DNA in a sample derived from a heterogeneous specimen (e.g., stool) contains a mutation associated with colorectal cancer. The 6th row is the threshold of detection of the assay used to measure PCR product after completion of PCR. That number is significant, as will be seen below, because sufficient mutant DNA must be produced by PCR to be detectable over aberrant signal from wild-type and random background noise. Under the heading "Outputs", the first line provides the likelihood that at least one mutant molecule is presented to the first round of PCR. The second line under the Output heading provides the likelihood of detection of mutants (after PCR) above the predetermined threshold for detection. For example, in experiment 4, the results indicate that in 87.9% of experiments run under the conditions specified for experiment 4, the number of mutants will exceed the threshold number for detection. Finally, the last two rows provide the coefficient of variation for sampling, and for the combination of sampling and PCR.

TABLE 1

| | 100% Efficiency PCR | | | | | | 20% Efficiency PCR | | | | | |
|---|---|---|---|---|---|---|---|---|---|---|---|---|
| | Exp 1 | Exp 2 | Exp 3 | Exp 4 | Exp 5 | Exp 6 | Exp 7 | Exp 8 | Exp 9 | Exp 10 | Exp 11 | Exp 12 |
| Inputs | | | | | | | | | | | | |
| Nominal number of Molecules going into PCR | 50 | 100 | 200 | 500 | 1,000 | 10,000 | 50 | 100 | 200 | 500 | 1,000 | 10,000 |
| Percent of molecules that are mutant | 1% | 1% | 1% | 1% | 1% | 1% | 1% | 1% | 1% | 1% | 1% | 1% |
| Number of PCR Rounds | 10 | 10 | 10 | 10 | 10 | 10 | 10 | 10 | 10 | 10 | 10 | 10 |
| Efficiency of PCR per round | 100% | 100% | 100% | 100% | 100% | 100% | 20% | 20% | 20% | 20% | 20% | 20% |
| Number of experiments modeled | 1,000 | 1,000 | 1,000 | 1,000 | 1,000 | 1,000 | 1,000 | 1,000 | 1,000 | 1,000 | 1,000 | 1,000 |
| M:W ratio which can be reliably detected by assay | 0.50% | 0.50% | 0.50% | 0.50% | 0.50% | 0.50% | 0.50% | 0.50% | 0.50% | 0.50% | 0.50% | 0.50% |
| Outputs | | | | | | | | | | | | |
| % of Experiments each with the number of mutant cells > 0 | 39.30% | 64.40% | 87.30% | 99.40% | 100% | 100% | 39.10% | 63.50% | 86.10% | 99.60% | 100% | 100% |

TABLE 1-continued

| | 100% Efficiency PCR | | | | | | 20% Efficiency PCR | | | | | |
|---|---|---|---|---|---|---|---|---|---|---|---|---|
| | Exp 1 | Exp 2 | Exp 3 | Exp 4 | Exp 5 | Exp 6 | Exp 7 | Exp 8 | Exp 9 | Exp 10 | Exp 11 | Exp 12 |
| % of Experiments each with number of mutant cells exceeding threshold | 39.30% | 64.40% | 87.30% | 87.90% | 97.10% | 100% | 36.20% | 52.40% | 63.30% | 63.30% | 91.60% | 100% |
| Stochastic Sampling CV | 143.20% | 100% | 70% | 44.10% | 32.10% | 9.90% | 144.60% | 101.80% | 72.00% | 44.20% | 32.00% | 10% |
| Stochastic Sampling and Stochastic PCRCV | 143.20% | 100% | 70% | 44.10% | 32.10% | 9.90% | 179.20% | 123.10% | 92.10% | 56.40% | 40.30% | 12.70% |

As shown in Table 1, even at 100% PCR efficiency, mutant DNA is detected in only 97.1% of the samples when 1000 input molecules are used (i. e, 1000 DNA molecules are available for priming at the initial PCR cycle), even though 100% of the DNA is amplified in any given round of PCR. When 10,000 molecules are presented, it is virtually certain that the mutant DNA will be amplified and detected, as shown in the results for experiment 6 in Table 1. Stochastic errors due to variation in the number of input molecules become less significant at about 500 input molecules and higher (i.e., the CV for stochastic variations is about the same regardless of whether PCR efficiency is 20% or 100%). At lower PCR efficiency (20% in Table 1), the model shows that introducing 50, 100, 200, 500, or even 1000 molecules into the PCR does not assure either amplification or detection. As shown in experiment 12, introducing 10,000 molecules results in amplification of the mutant target, and a high likelihood of its subsequent detection. Thus, even with 100% efficient PCR, significant false negative events occur when input molecules fall below 500.

The foregoing analysis shows that there is a unique range for the number of molecules that must be presented to a PCR in order to achieve amplification of a low-frequency DNA, and to allow its detection. That range is a function of the PCR efficiency, and the percentage of low-frequency (mutant) DNA in the sample, and the detection threshold. The aforementioned model was developed and run in Visual Basic for Applications code (Microsoft, Office 97) to simulate a PCR as described above. The statistical confidence level within which results were measured was held constant at approximately 99%. Only the PCR efficiency and percent mutant DNA were varied. As discussed above, the model iteratively samples DNA in a "Monte Carlo" simulation over a thousand experiments, each experiment consisting of 10 rounds of PCR. The results are shown below in Table 2.

TABLE 2

| | Number of molecules needed | | | |
|---|---|---|---|---|
| PCR Efficiency | 1% Mutant | 2% Mutant | 5% Mutant | 10% Mutant |
| 10% | 3,000 | | | |
| 20% | 2,500 | | | |
| 50% | 2,200 | | | |
| 100% | 1,600 | | | |
| 10% | | 1,500 | | |
| 20% | | 1,200 | | |
| 50% | | 1,000 | | |
| 100% | | 800 | | |
| 10% | | | 500 | |
| 20% | | | 450 | |
| 50% | | | 400 | |
| 100% | | | 300 | |
| 10% | | | | 225 |
| 20% | | | | 200 |
| 50% | | | | 150 |
| 100% | | | | 125 |

Regression of the data obtained using the model as described above produced the set of curves set forth below in FIG. 5.

Figure 5:
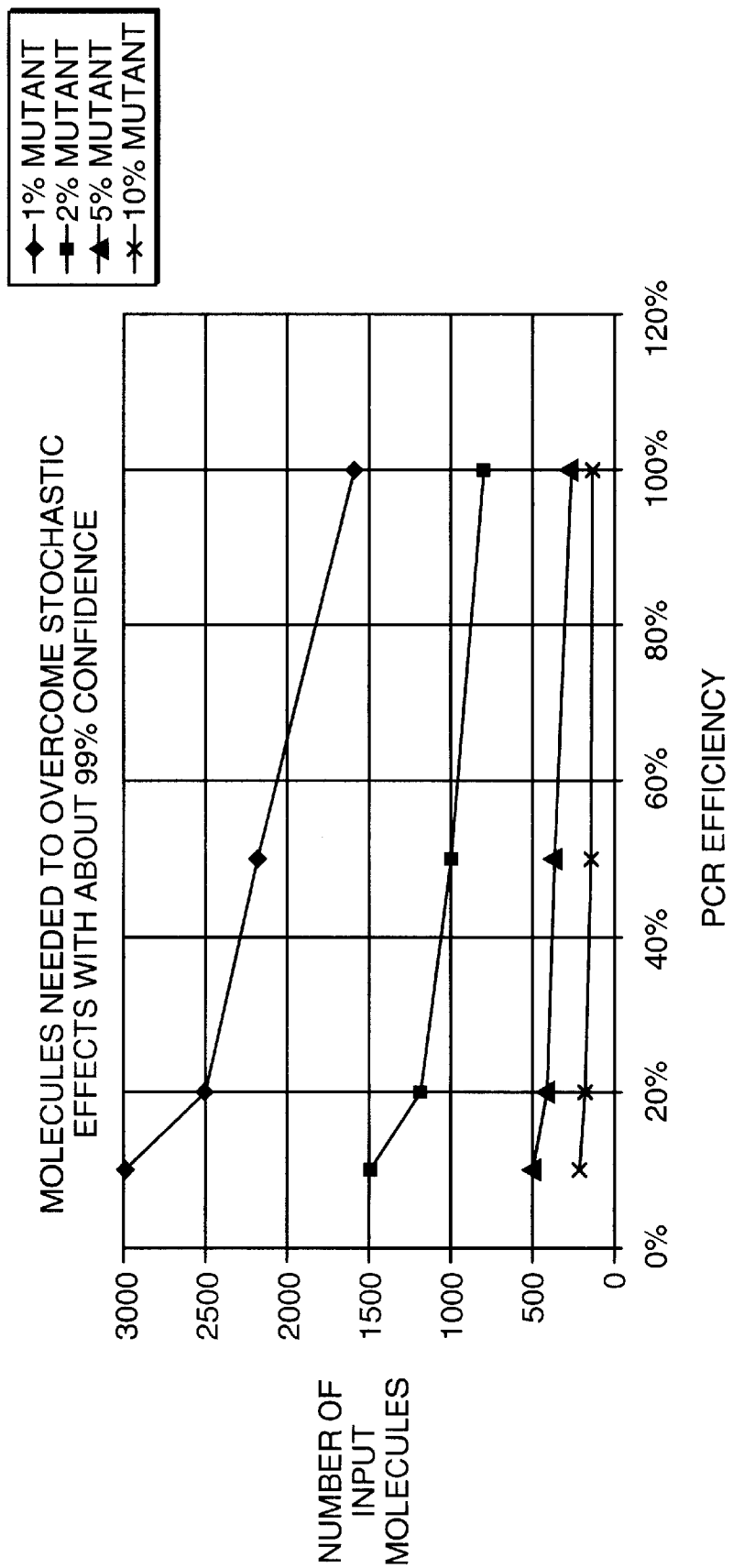
FIG. 5 shows a set of curves produced by regression analysis of the data obtained using the model as described for, for example, Tables 1 and 2.

Using FIG. 5, the optimal number of molecules to be presented to the PCR is determined by selecting a PCR efficiency (or determining the efficiency by empirical means), and selecting a percentage of the sample suspected to be mutant DNA associated with disease. This, in turn, dictates a threshold of detection. Not all detection strategies have similar underlying detection thresholds, so an appropriate technology must be selected. The percentage mutant DNA may be determined by clinical considerations as outlined above for colorectal cancer.

One may determine the PCR efficiency and percent expected mutant in order to maximize the probability of obtaining amplified, detectable mutant DNA. For example, one may select N, the number of input molecules from the "1%" curve in FIG. 5, when 5% of the sample is expected to be mutant DNA in order to increase the confidence of the assay result.

This model, and particularly FIG. 5, are useful when determining optimal concentrations of a DNA degradation inhibitor. If PCR is used to analyze DNA after the DNA sample is exposed to a DNA inhibitor, FIG. 5, will indicate how many molecules of target DNA need to be preserved in order to have sufficient analyzable DNA. Thus, the optimal amount of any DNA degradation inhibitor may be determined as that amount, or range of amounts, of inhibitor that produce a sufficient number of analyzable DNA according to FIG. 5. Of course, this modeling system may be applied to DNA detection techniques other than PCR. Specifically, those skilled in the art can apply this modeling system to any process and/or detection technique in which stochastic noise is problematic. Thus, the optimal amount of any DNA degradation inhibitor can be determined based upon the number of DNA molecules that are sufficient to produce analyzable DNA.

Once the number of molecules for input to the PCR is determined, a sample comprising that number of molecules (or greater) is prepared for PCR according to standard methods. The number of molecules in a sample may be determined directly by, for example, enumerative methods such as those taught in U.S. Pat. No. 5,670,325, incorporated by reference herein. Alternatively, the number of molecules in a complex sample may be determined by molar concentration, molecular weight, or by other means known in the art. The amount of DNA in a sample may be determined by mass spectrometry, optical density, or other means known in the art. The number of molecules in a sample derived from a biological specimen may be determined by numerous means in the art, including those disclosed in U.S. Pat. Nos. 5,741,650 and 5,670,325 both of which are incorporated by reference herein.

Methods as described above are used to determine minimum or optimal amounts of DNA degradation inhibitors for use in any DNA isolation, detection, or amplification process in which stochastic processes occur. Using the above-described model for determining the minimum number of molecules that must be measured to reliably detect a low-frequency species, one can empirically determine how much of any given inhibitor should be used.

II. Example—Detection of DNA in Stool with EDTA as a DNA Degradation Inhibitor

A. Introduction

Methods of the invention are useful for analyzing DNA from stool to detect colorectal cancer. If colorectal cancer is diagnosed early, it may be treated effectively by surgical removal of the cancerous tissue. Colorectal cancers originate in the colorectal epithelium, and typically are not extensively vascularized (and therefore not invasive) during the early stages of development. The transition to a highly vascularized, invasive and ultimately metastatic cancer which spreads throughout the body commonly takes ten years or longer. If the cancer is detected prior to invasion, surgical removal of the cancerous tissue is an effective cure. However, colorectal cancer is often detected only upon manifestation of clinical symptoms, such as pain and black tarry stool. Generally, such symptoms are present only when the disease is well established, often after metastasis has occurred, and the prognosis for the patient is poor, even after surgical resection of the cancerous tissue. Early detection of colorectal cancer, therefore, is important because early detection may significantly reduce patient morbidity.

B. Experiments

The following experiments demonstrate that EDTA, an inhibitor of DNase, increases the yield of high-integrity DNA from a stool sample with a concomitant increase in the amount of amplifiable DNA. In these experiments, three aliquots of stool (5 g each) were homogenized in buffer (0.5 M Tris, 10 mM NaCl, EDTA). The buffer to stool ratio was 7:1; thus, 35 ml of buffer was used for each 5 g of stool. The buffer contained either 0 mM EDTA, 16 mM EDTA, or 96 mM EDTA. Each of the three aliquots was then diluted with additional buffer (not containing EDTA) to a final buffer to stool ratio of 20:1. Each aliquot was then centrifuged, and the supernatant, which carried the active DNA degrading fraction, was removed to a clean tube. Then, a DNA mixture of 2 $\mu$g E. coli DNA and 100 ng human genomic DNA was added to each tube. Each tube was incubated for 75 minutes at 37° C. Then, 42 $\mu$l of Proteinase K and 250 $\mu$l of 10% SDS (sodium dodecyl sulfate) were added to each tube followed by an overnight incubation at 37° C. After the overnight incubation, the DNA in each sample was prepared by standard techniques. See, e.g., SHORT PROTOCOLS IN MOLECULAR BIOLOGY §§2.1–2.4 (Ausubel et al., 3d ed., 1995). Generally, a phenol extraction, a phenol/chloroform extraction, and a phenol extraction were performed prior to isolating the DNA. Then, the isolated DNA was placed into a standard Tris buffer.

Figure 2:
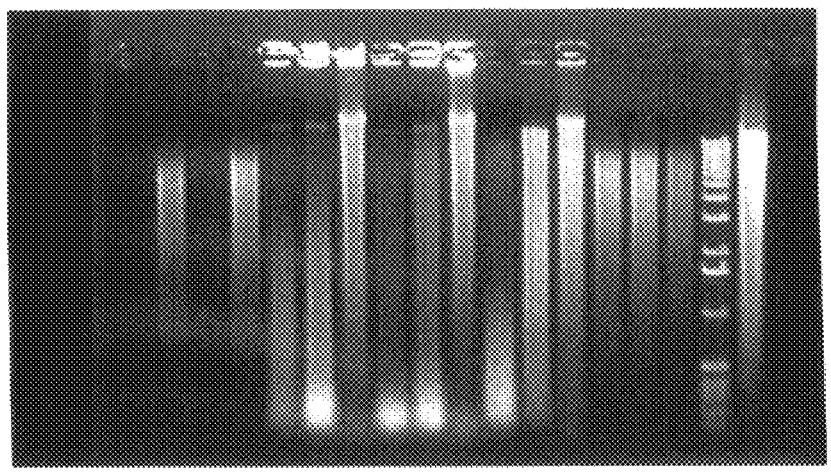
FIG. 2 shows a separation gel of DNA isolated from several different homogenized stool supernatants that contained various concentrations of EDTA.

Three experiments were conducted on the isolated DNA. The first experiment demonstrated that the DNA degrading activity present in homogenized stool supernatant is inhibited by optimal amounts of EDTA, increasing the amount of high-integrity DNA. In this experiment, DNA was isolated from homogenized stool supernatant which was taken from aliquots of stool homogenized in buffer having 0 mM, 16 mM, or 96 mM EDTA. Total nucleic acid was run on a separation gel. Results are shown in FIG. 2, where arrows identify the location of the smear (or lack thereof) containing the DNA of interest.

Lanes 4, 5, and 6 represent samples of DNA added to homogenized stool supernatant, obtained from stool homogenized in buffers containing 0 mM, 16 mM, or 96 mM EDTA, respectively, that was subsequently isolated. Note that each lane shows a high molecular weight band which represents endogenous DNA from the stool sample and a smear from the exogenous DNA. The intensity of the band and smear in the photograph (which correlates with the amount of DNA in the band, a greater intensity corresponding to a greater amount of DNA) increased as the concentration of EDTA in the original buffer increased. Lanes 7–9 and 10–12 are replicates of lanes 4–6. The increasing intensity of the bands and the smears as EDTA concentration increased indicated that DNA integrity was preserved as the concentration of EDTA in the buffer increased. Thus, the DNA degrading activity of the homogenized stool supernatant was inhibited by the EDTA in a roughly dose-dependent manner.

Lanes 1, 2 and 3 and lanes 13, 14 and 15 were control samples containing 2 $\mu$g E. coli DNA and 100 ng exogenous human DNA in buffer made with 16 mM EDTA. As expected, each lane showed a smear representative of the added DNA.

Figure 3:
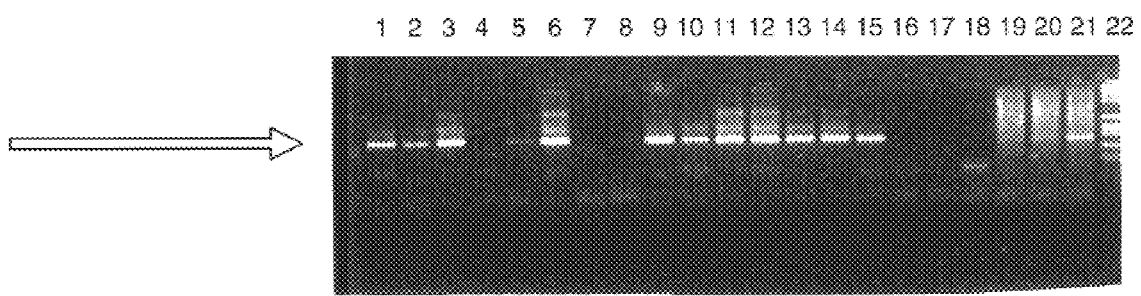
FIG. 3 shows a separation gel of DNA isolated from homogenized stool supernatant that contained various concentrations of EDTA followed by capture and amplification.

In a second experiment, the isolated DNA as described above was captured and amplified. The results of this experiment demonstrated that EDTA not only inhibits the DNA degrading activity present in stool supernatant but also increases the amount of amplifiable DNA. In this experiment, after preparing the DNA as described above, a standard hybrid capture was performed using Kras-specific capture probes to capture Kras DNA. The Kras DNA then was PCR amplified. FIG. 3 shows the effect of EDTA on the preservation of Kras DNA. The location of the band (or lack thereof) representing Kras DNA is identified with an arrow.

Lanes 4, 5, and 6 represent Kras DNA that was amplified from template DNA that was added to homogenized stool supernatant obtained from stool homogenized in buffer containing 0 mM, 16 mM, or 96 mM EDTA, respectively. Note that the Kras band in lane 4 was nearly absent, while the Kras band grew in intensity (representing an increase in the amount of Kras DNA actually present) in lanes 5 and 6 as the concentration of EDTA in the buffer increased. Lanes 7–9 are replicates of lanes 4–6 and show a similar increase in band intensity (an increase in the amount of DNA present) as the concentration of EDTA in the original buffer increased. Thus, more Kras DNA was amplified, resulting in a more robust signal at higher concentrations of EDTA.

Additionally, in the population, levels of DNA which can be amplified from stool vary across individuals. These individuals have been characterized in groups from A to F, with A being the highest level of DNA and F being an undetectable level of DNA. The high levels of DNA in group A are due to low DNA degradation activity in their stool ("high-integrity stool"). Adding EDTA to the buffer in which a stool aliquot from a Group A individual is homogenized would not be expected to produce a large effect because Group A stool has little DNA degrading activity. In fact, when Kras DNA was amplified from template DNA that was added to homogenized stool supernatant obtained from Group A stool homogenized in buffer containing 0 mM, 16 mM, or 96 mM EDTA, little difference in the amount of amplified Kras DNA was observed (lanes 10, 11, and 12, respectively). Only a slight increase in Kras band intensity can be seen between 0 mM EDTA and 16 mM or 96 mM EDTA, representing only a slight increase in the amount of Kras DNA at inhibitory concentrations of EDTA.

Lanes 1–3 as well as lanes 13–15 represent samples of amplified Kras DNA that was not exposed to homogenized stool supernatant. As expected, those control lanes show a band of equal intensity across lanes representing Kras DNA. Lanes 16 and 17 are negative controls and, as expected, show no band representing Kras, indicating that any observed Kras DNA is due to captured DNA and not to contamination. Lane 18 is a negative control, and, as expected, has no band representing the Kras gene, indicating that the PCR products are from the sample and not from contamination. Lanes 19–21 are positive controls where 50 pg, 100 pg, or 200 pg of human DNA is amplified in a background of E. coli DNA, indicating that human DNA can be amplified in an E. coli background in this model system. Finally, lane 22 is a molecular weight marker.

Figure 4:
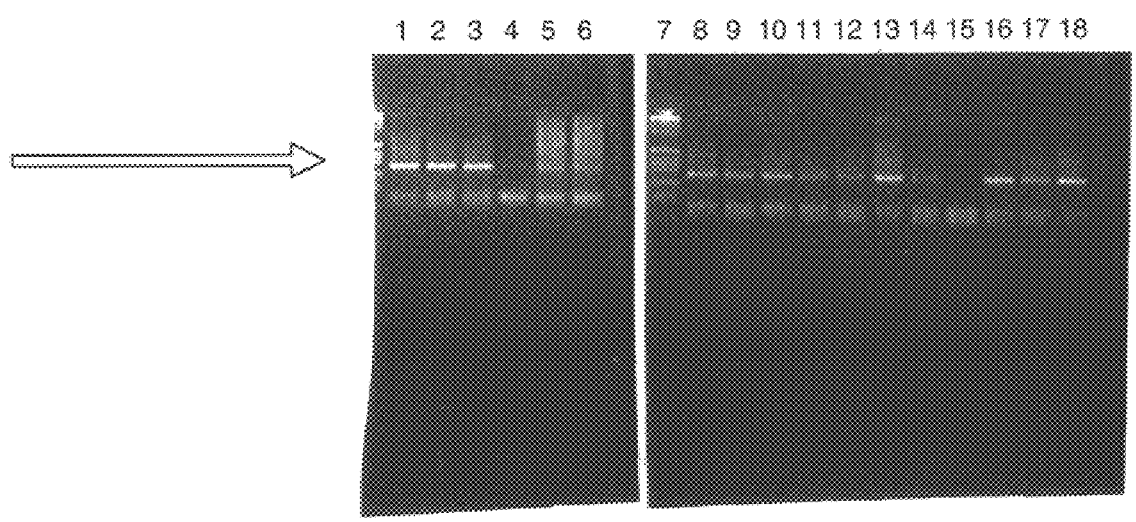
FIG. 4 shows separation gel of DNA isolated from homogenized stool supernatant that contained various concentrations EDTA followed by capture, addition of more DNA, and amplification.

In a third experiment, the same protocol was used as in the second experiment except human genomic DNA was added into each sample after capture. Kras DNA was again amplified by PCR. Thus, an excess of template DNA was available for PCR. This experiment demonstrated that the varying levels of PCR amplification in the second experiment were not due to EDTA interfering with or enhancing normal PCR but were due to varying levels of template DNA available to be amplified resulting from various levels of DNA degradation inhibition by EDTA. FIG. 4 shows the results of this experiment. The location of the band (or lack thereof) representing Kras is identified with an arrow. Lanes 1–6 and 8–13 correspond with lanes 1–12 in the second experiment (i.e., lanes 1–3 were controls, lanes 4–6 and 8–10 were excess Kras DNA amplified in samples exposed to homogenized stool supernatant from stool homogenized in 0 mM, 16 mM, or 96 mM EDTA, and lanes 11–13 were excess Kras DNA amplified in samples exposed to homogenized stool supernatant from high-integrity stool homogenized in 0 mM, 16 mM, or 96 mM EDTA). As expected, lanes 1–6 and 8–13 show a PCR product of roughly equal intensity because an excess of template DNA is available. The EDTA does not interfere with or enhance normal PCR. This result indicates that the varying levels of PCR amplification in the 0 mM, 16 mM, or 96 mM EDTA samples in the second experiment was due to varying levels of template DNA and not to inhibitor. Lane 14 shows a sample of human genomic DNA. Lanes 15–18 are the same controls as lanes 17 and 19–21 in the second experiment.

From the experimental data described above, the amount of EDTA required to inhibit DNase was calculated. The concentration of EDTA in the various buffers used in the three experiments was normalized as grams of EDTA per gram of stool. Generally, the concentration of EDTA was multiplied by the molecular weight of EDTA and by the volume of buffer in which the stool was homogenized. The product was divided by the amount of stool that was homogenized. For example, the following equations were used to normalize EDTA concentration.

For 16 mM EDTA:

(0.016 EDTA M/L×372.2 g/M×0.035L) ÷5 g=0.042 g EDTA per gram of stool

For 96 mM EDTA:

(0.096 EDTA M/L×372.2 g/M×0.035L) ÷5g=0.250 g EDTA per gram of stool

Thus, for any amount of stool to be homogenized, at least about 0.042 g EDTA per gram of stool should be used in the homogenization buffer in order to maximize yield of DNA. The range of EDTA which may be used is from about 0.042 g EDTA per gram of stool to about 0.782 g EDTA per gram of stool. More preferably, about 0.250 g EDTA per gram of stool to about 0.521 g EDTA per gram of stool is used. Most preferably, about 0.391 g EDTA per gram of stool is used.

These calculations indicate that at commonly used buffer volumes and stool amounts, the amount of EDTA present in the homogenized sample is a more important factor than the final concentration of EDTA in the homogenized sample. However, as one skilled in the art realizes, at some point, although the amount of EDTA will remain the same in a given volume, the volume may become so large that the effect of EDTA on DNA integrity is diluted. When examining a stool sample within commonly used parameters, this dilution effect is not seen. However, in alternative embodiments, the concentration of EDTA is a relevant factor. In these embodiments, from about 16 mM EDTA to about 300 mM EDTA is useful. More preferably, from about 100 mM EDTA to about 200 mM EDTA is useful. Most preferably, about 150 mM EDTA is useful.

What is claimed is:

1. A method for preserving the integrity of DNA in a stool sample, the method comprising:

exposing the stool sample to EDTA in a range from about 0.250 gram EDTA per gram of stool to about 0.782 gram EDTA per gram of stool to preserve the integrity of DNA.

2. The method of claim 1 further comprising a step of extracting a target DNA.

3. The method of claim 2 wherein the step of extracting comprises a phenol-chloroform extraction.

4. A method for preserving the integrity of DNA in a sample containing exfoliated cells, the method comprising:

exposing the sample to EDTA in a range from 0.250 gram EDTA per gram of sample to about 0.782 gram EDTA per gram of sample to preserve the integrity of DNA.

5. The method of claim 4 wherein the sample is obtained from stool.

6. The method of claim 4 further comprising extracting a target DNA.

7. The method of claim 6 wherein the step of extracting comprises a phenol-chloroform extraction.

8. The method of claim 1 comprising exposing the sample to EDTA in a range from about 0.250 gram EDTA per gram of stool to about 0.521 gram EDTA per gram of stool to preserve the integrity of DNA.

9. The method of claim 1 comprising exposing the sample to about 0.391 gram EDTA per gram of stool to preserve the integrity of DNA.

10. The method of claim 4 comprising exposing the sample to EDTA in a range from about 0.250 gram EDTA per gram of sample to about 0.521 gram EDTA per gram of sample to preserve the integrity of DNA.

11. The method of claim 4 comprising exposing the sample to about 0.391 gram EDTA per gram of sample to preserve the integrity of DNA.

* * * * *